United States Patent [19]

Economy et al.

[11] 4,273,906

[45] Jun. 16, 1981

[54] POLYMERIZABLE ACETYLENIC OLIGOMERS

[75] Inventors: James Economy; Mary Ann Flandera, both of San Jose, Calif.

[73] Assignee: International Business Machines Corporation, Armonk, N.Y.

[21] Appl. No.: 132,245

[22] Filed: Mar. 20, 1980

Related U.S. Application Data

[63] Continuation-in-part of Ser. No. 956,517, Oct. 31, 1978, abandoned.

[51] Int. Cl.$^3$ .......................... C08F 4/50; C08F 38/00; C08F 238/00
[52] U.S. Cl. ................................. 526/285; 526/217; 526/221
[58] Field of Search .................... 526/221, 285, 217

[56] References Cited

U.S. PATENT DOCUMENTS

| | | | |
|---|---|---|---|
| 3,300,456 | 1/1967 | Hay | 526/285 |
| 4,020,265 | 4/1977 | White | 526/285 |
| 4,070,333 | 1/1978 | Jabloner | 526/285 |
| 4,108,942 | 8/1978 | Chalk et al. | 526/285 |

Primary Examiner—John Kight, III
Attorney, Agent, or Firm—Joseph G. Walsh

[57] ABSTRACT

Soluble, polymerizable oligomers having a number average molecular weight of from about 200 to about 10,000, are obtained by treating triethynylbenzene with an oxygen-carrying, amine-basic cupric salt complex catalyst in the presence of a molar excess over the monomer of an aromatic monacetylenic capping agent. The oligomers are used to form polymers which are adhesives and coatings.

4 Claims, No Drawings

POLYMERIZABLE ACETYLENIC OLIGOMERS

The present application is a continuation in part of our copending application Ser. No. 956,517, filed Oct. 31, 1978 abandoned.

DESCRIPTION

1 Technical Field

This invention is concerned with polymerizable, processable oligomers. In particular it is concerned with soluble, polymerizable oligomers having a number average molecular weight of from about 200 to about 10,000. The oligomers are obtained by treating triethynylbenzene with an oxygen-carrying, amine-basic cupric salt complex catalyst in the presence of a molar excess over the monomer of an aromatic monoacetylenic capping agent.

It is an object of the present invention to prepare prepolymers which are storable for long periods of time, but which are readily processable into useful adhesive films which are curable without the evolution of gas. This object is achieved by control of the reaction of triethynylbenzene with an aromatic monoacetylenic capping agent.

2. Background Art

U.S. Pat. No. 3,300,456 of Hay describes the preparation of acetylenic polymers by the self-condensation reaction resulting from the oxidative coupling of organic compounds containing at least two terminal acetylenic groups directly bonded to the organic nucleus. The Hay process comprises reacting such compounds with oxygen in homogeneous solution in the presence of a dissolved oxygen-carrying intermediate comprising an amine-basic cupric salt complex. According to the Hay patent, when his starting material contained three or more terminal acetylenic groups, his product was a three-dimensional cross-linked, insoluble, infusible polymer. (See U.S. Pat. No. 3,300,456, Col. 2, lines 51–54.) Furthermore, he reports that his polymers decompose at about 180° C. (Col. 7, line 60.)

U.S. Pat. No. 4,070,333 of Jabloner describes prepolymers from triethynylbenzene. The prepolymers are to be used as part of a molding composition, and they are obtained by use of a nickel containing aromatization catalyst very different in structure and effect from the catalyst used in the present invention. No diacetylenic units are contained in the resulting prepolymer.

DISCLOSURE OF THE INVENTION

The present invention is in sharp contrast to this prior work of Hay and of Jabloner. According to the present invention, there are obtained from triethynylbenzene processable polymerizable oligomers. These oligomers are prepolymers which, when polymerized, undergo cross-linking and yield polymers which have many desirable and unexpected properties. The oligomers can be processed into coatings and adhesive bonds by a wide variety of coating techniques, for example, either from a solution or from a melt. When the prepolymers are advanced by heating above about 140° C., they yield polymers having many desirable and unexpected properties. During this heating cycle, there is essentially little or no gas evolved, which is a very desirable property for adhesives. These oligomers can also be cured by irradiation, such as ultra violet or electron beam radiation. The films are very adherent to a variety of substrates, and can be heated up to over 400° C. in nitrogen with little or no loss in properties. They are very stable and moisture resistant, and are also resistant to both acid and to base. The oligomers of the present invention may be stored, and then polymerized.

In the process of forming the oligomers of the present invention, it is essential that the molecular weight of the product be carefully controlled. This is done by proper choice of the amine used in the reaction, in some cases by using a reverse addition of the catalyst to the monomer, by controlling the rate of addition of the catalyst, and, most significantly, by regulating the amount of monoethynyl capping agent. Thus, in the present invention, workable, useful oligomer pre-polymers are obtained.

The capping agent referred to above is an aromatic monoethynyl compound, for example, phenylacetylene. The single ethynyl group of the capping agent enters into the coupling reaction, but because the molecule has only one ethynyl group, further coupling is stopped. It is a critical feature of the present invention that the molecular weight of the oligomer is controlled by using a molar excess of an aromatic monoethynyl capping agent. This capping also provides the oligomer with a group sensitive to both ultra violet and electrom beam irradiation, so that it may be cross-linked. By increasing the amount of capping agent, the molecular weight of the prepolymer is decreased. Increasing the amount of the capping agent also increases the amount of diacetylenic groups, and leads to a higher cure temperature for the prepolymer. It is preferred that at least 60% of the acetylenic groups are diacetylenic. It is also preferred that each oligomer molecule contain at least two diacetylenic groups.

The most preferred aromatic monoacetylenic capping agent is phenylacetylene. Other useful compounds include those having halogen, lower alkyl or lower alkoxy substituents on the phenyl ring of phenylacetylene. Multiple aromatic ring systems may also be used.

The oligomers of the present invention are readily processable into films and coatings because of their good solubility in a number of common solvents. On the other hand, when they are converted to polymers, upon curing they are converted into highly insoluble materials. The effect of branching facilitates solubility and film formation enabling a higher MW to be achieved and therefore better mechanical and film characteristics. Linear type systems, due to their rigidity, tend to crystallize and lack sufficient solubility in common solvent for usual processing.

In the formulations of the oligomers for end use, it is to be understood that they are to be used like other prepolymers, such as phenolic and epoxies, in that fillers, reinforcements and plasticizers can be incorporated over a wide range of concentrations as desired.

The following Examples are given solely for the purposes of illustration, and to demonstrate the preferred mode of carrying out the invention.

EXAMPLE 1

Poly (1,3,5-triethynyl benzene)

Prepolymer I (0–5% ethynyl content)

1,3,5-triethynyl benzene 5 g, (0.033 moles) and 51 g (0.485 moles) of phenylacetylene were mixed with 50 ml acetone and added slowly to a catalyst solution composed of 2.97 g, 0.03 moles CuCl, 4.52 ml, 0.03 moles tetramethylethylene diamine in 250 ml acetone (1:1 molar ration, 5% of total C≡C—H). The catalyst solution was pre-oxidized by bubbling $O_2$ through for several minutes before the addition. The reaction mixture was stirred vigorously for the extent of the reaction, i.e. 8 hours.

The solvent was reduced to ½ volume and the slurry poured onto acidified methanol. (3000 ml MeOH, 20 ml conc HCl.) The precipitate was collected and washed with methanol until there was no detectable acid. The by-product diphenyl diacetylene is soluble in MeOH and is washed out. The prepolymer is dissolved in $CHCl_3$ and passed through a short silica gel (30μ mesh) column to remove insoluble/gel material. The $CHCl_3$ solution was concentrated and poured onto MeOH. The polymer was collected, dried, and yielded 11.0 g of a creamy white solid.

Characterization: (Prepolymer 0–5% C≡C—H content)

LC: Liquid chromatography using a μ-$C_{18}$ Bondapak reversed-phase column using 78% $THF/H_2O$ to elute. The distinctive pattern of thirteen peaks with alternate peaks minimal or absent characterize this material.
NMR: Multiplet 7.2–7.6 δ no C≡C—H detectable
TGA: No weight loss until 500° C. with 5% loss at 800° C. under helium.
IR: C≡C—H stretch in this case is very small.
M.W.: GPC 200—5000 ranges, most material having M.W.≦2000 with a long tail to 8,000. VPO Mn=557.
DSC: Two exothermic peaks with maxima at 150° C., 200° C.
UV: The optical absorption spectrum for this material has an absorption envelope from 370 nm to 200 nm with principal absorption maxima at 296 nm, 314 nm and 336 nm.

All three types of polymers based on poly(TEB) have similar spectrum with a slight shift to longer λ with degree of capping.

It is estimated that in this prepolymer the ratio of diacetylenic groups to aromatic rings was in the range of about 95% to 100%.

EXAMPLE 2

Poly (1,3,5-triethynyl benzene)

Prepolymer II (6–20% ethynyl content)

1,3,5-triethynylbenzene 5.0 g (0.033 mole) and 30.6 g (0.30 mole) of phenylacetylene were mixed in 50 ml acetone and added slowly to a vigorously stirred catalyst solution consisting of 4.25 g (0.043 moles) CuCl and 6.93 ml, (0.086 mole) pyridine (1:2 molar ratio, 10% of total ethynyl content). Only one-half of the amount of catalyst was present for the first three hours. The catalyst solution was pre-oxidized by bubbling $O_2$ through for several minutes before addition. The reaction was allowed to continue from 12–18 hours. The workup is identical to Example 1, and yielded 7.7 g of creamy-white polymer.

Characterization

LC: On a μ-$C_{18}$ Bondapak reverse phase liquid chromatograph column using 78% $THF/H_2O$ thirteen peaks identified by UV detection (λ=254 nm) of which alternate peaks are approximately one-half the height from a gaussian distribution.
NMR: Multiplet (aromatic 7.2–7.6 δ Singlet (C≡C—H)=3.1 δ integrated ratio 3/104 or 12% ethynyl/aromatic ring.
TGA: No weight loss 500° C., 5% weight loss at 750° C. under helium.
DSC: Principal exothermic peaks 155° C., 200° C.
IR: 3304 $cm^1$ (C≡C—H), 3080 $cm^{-1}$ (aromatic), 2220 $cm^{-1}$ (—C≡C—) 1850 $cm^{-1}$ (1.3.5 tri and mono substituted benzene), 1490 $cm^{-1}$, 1445 $cm^{-1}$ (mono substituted benzene), 1418 $cm^{-1}$ (1.3.5 tri and mono substituted benzene)
UV: Similar to Example 1, slight increase in tail of 330 nm peak.
MW: Gel permeation chromatography using 2×500 Å μ-styragel columns gave a molecular weight range from 200–8000 with principle components 2000 or less. Vapor Phase Osmometry: produced a Mn of 587.

This polymer, with an intermediate degree of capping, is easily coated from common organic solvents. The material with heat (250° C. cure for 3 hours) to an insoluble material capable of withstanding base or acid soaks. The film is highly adherent even after heating to 375° C.

It is estimated that in this prepolymer the ratio of diacetylenic groups to aromatic rings is in the range of from 75% to 95%.

EXAMPLE 3

Poly (1,3,5-triethynylbenzene)-Prepolymer III (30%–80% of ethynyl content)

10 g, (0.067 moles) of 1,3,5 triethynylbenzene and 68.3 g, (0.067 moles) of phenylacetylene were mixed in acetone and added slowly to a vigorously stirred catalyst solution consisting of 8.6 g. (0.087 moles), CuCl and 7 ml pyridine (0.087 moles) 01:1 molar ration, 10% of total ethynyl content) in which one-half the catalyst was present for the first 3-4 hours. The catalyst was pre-oxidized before addition. The reaction was allowed to proceed for 24 hours, at which time no trace of 1,3 5-triethynylbenzene was present by TLC (thin layer chromotography).

Workup identical to Examples 1 and 2 and yielded 10.0 g of light yellow polymer.

Characterization

LC: Using identical column and conditions, the thirteen peaks yield a gaussian pattern, including alternate peaks.
NMR: 7.2–7.6 δ (aromatic) 3.1 δ (ethynyl). Integrated ratio 10/112 (ethynyl)/aromatic or 40% ethynyl-/aromatic ring.
TGA: Stable to 500° C. under helium.
DSC: Principle exothermic peaks 140° C., 165° C.
IR: (C≡CH) 3300 $cm^{-1}$, (Aromatic) 2940 $cm^{-1}$, 2220 $cm^{-1}$ (Diacetylene) etc. The C≡C—H absorption at 3300 $cm^{-1}$ is much larger than other examples.
UV: Similar to Example 1, increase in tail of 336 nm peak.
MW; Gel permeation chromatography. Molecular range of 200–8000 with most material ≦2000.

It is estimated that in this prepolymer the ratio of diacetylenic groups to aromatic rings is in the range of from 66% to 95%.

We claim:

1. A soluble, polymerizable oligomer having a number average molecular weight of from about 200 to about 10,000 obtained by reacting triethynylbenzene with an oxygen-carrying amine-basic cupric salt complex catalyst in the presence of a molar excess over the monomer of an aromatic monoacetylenic capping agent.

2. An oligomer as claimed in claim 1 in which the molecular weight is from about 400 to about 2,000.

3. An oligomer as claimed in claim 1 which contains at least two diacetylene groups.

4. An oligomer as claimed in claim 1 in which the capping agent is phenylacetylene.

* * * * *